United States Patent [19]
Arnaud-Battandier et al.

[11] Patent Number: 5,952,295
[45] Date of Patent: Sep. 14, 1999

[54] COMPOSITION AND METHOD FOR TREATMENT OF INFLAMMATORY CONDITIONS OF THE GASTRO-INTESTINAL TRACT

[75] Inventors: Franck Arnaud-Battandier, Le Chesnay; Etienne Alfred Grasset, Boulogne Billancourt, both of France; Véronique Jaussan, Morges, Switzerland

[73] Assignee: Nestec S.A., Vevey, Switzerland

[21] Appl. No.: 09/003,269

[22] Filed: Jan. 6, 1998

[30] Foreign Application Priority Data

Jan. 14, 1997 [EP] European Pat. Off. ............ 97200096

[51] Int. Cl.⁶ .................................................. A01M 37/18
[52] U.S. Cl. .................... 514/2; 514/2; 514/12; 514/23; 514/547
[58] Field of Search .................. 514/2, 12, 23, 514/547, 560, 681, 643, 474, 702, 578, 556, 763

[56] References Cited

U.S. PATENT DOCUMENTS 5,461,033  10/1995  Donnet et al. ............................ 514/12
5,661,123  8/1997  Stalker et al. ............................ 514/2

FOREIGN PATENT DOCUMENTS 0 313 515  4/1989  European Pat. Off. .
0 527 283  2/1993  European Pat. Off. .

OTHER PUBLICATIONS

Beattie et al., "Polymeric Nutrition as the Primary Therapy in Children with Small Bowel Crohn's Disease", *Alimentary Pharmacology & Therapeutics*, vol. 8, 1994, pp. 609–615.

Sanderson et al., "Remission Induced by an Elemental Diet in Small Bowel Crohn's Disease", *Archives of Disease in Childhood*, vol. 61, 1987, pp. 123–127.

Giaffer et al., "Controlled Trial of Polymeric Versus Elemental Diet in Treatment of Active Crohn's Disease", *The Lancet*, vol. 335, Apr. 7, 1990, pp. 816–819.

Derwent Abstract AN 97–231148–JP 950254630.

*Primary Examiner*—F. T. Moezie
*Attorney, Agent, or Firm*—Hill & Simpson

[57] ABSTRACT

An enteral, nutritional composition for the treatment or prophylaxis of inflammatory conditions of the gastro-intestinal tract; for example Crohn's disease. The composition contains: (i) casein rich in TGF-$\beta 2$; (ii) a lipid source which provides about 35% to about 50% of energy; and (iii) a carbohydrate source.

23 Claims, 4 Drawing Sheets

COMPOSITION AND METHOD FOR TREATMENT OF INFLAMMATORY CONDITIONS OF THE GASTRO-INTESTINAL TRACT

FIELD OF THE INVENTION

This invention relates to an enteral, nutritional composition which may be used in the treatment or prophylaxis of inflammatory conditions of the gastro-intestinal tract; for example Crohn's disease. The invention also relates to a method for the treatment and prophylaxis of inflammatory conditions of the gastro-intestinal tract.

BACKGROUND OF THE INVENTION

Inflammatory conditions of the gastro-intestinal tract often cause severe discomfort, abdominal pain and diarrhoea to suffers. Further, persons with these conditions often have an impaired ability to take up nutrients. This is particularly serious in children where it can lead to stunted growth and poor weight gain. Examples of these conditions are Crohn's disease, ulcerative colitis, and certain infectious diseases such as AIDS. Of these conditions, Crohn's disease is particularly troublesome. The disease may cause severe abdominal pain and nutritional problems. Also, the disease has a high relapse rate after treatment. For example, in children, Crohn's disease has a chronic relapsing course in which up to 50% of the patients eventually need surgery (Davies, G et al; 1990; Br. J. Surg.; 77: 81–94).

Treatment of Crohn's disease using corticosteroid therapy is found to induce remission and is a treatment which is often used. However, corticosteroid therapy has undesirable side effects; particularly in children where growth is adversely affected. Cyclosporin has also been attempted in the treatment of Crohn's disease but the side effects of Cyclosporin are particularly severe; especially on renal function and reduced immune response.

Consequently, there has been considerable interest in the use of nutritional therapy in the treatment or prophylaxis of Crohn's disease. In particular, the semi-elemental formula, Flexical® (Mead Johnson), has been shown to be as effective as the steroid prednisolone (Sanderson et al; 1987; Arch. Dis. Child.; 51: 123–7). Since the publication of this report, Flexical®, and other similar semi-elemental formulas, have often been used as a primary therapy in Crohn's disease. However, semi-elemental formulas, which are based upon hydrolysed protein, are relatively expensive and often suffer from palatability problems. This has restricted their use.

Attempts have therefore been made to use whole protein in nutritional therapy of Crohn's disease. However, the treatment has not been universally successful (Giafer et al; 1990; Lancet; 335:816–9). To improve the efficacy of the formulas, efforts have recently focused on the type of protein used in the formulas. For example, U.S. Pat. No. 5,461,033 describes the use of an acid casein fraction, which is isolated from bovine milk and which contains TGF-β2, in the treatment of Crohn's disease. The data reported in the patent are based upon in vitro experimentation and the patent gives no specific description of nutritional formulas which may be used in the treatment of Crohn's disease. However, Beattie et al (1994; Aliment. Pharmacol. Ther.; 8: 1–6) have reported the use of the acid casein fraction in an infant formula in the treatment of 7 children with active small bowel Crohn's disease. The energy content of the formulation was 700 Kcal/l, the osmolality was 150 mOsm/l, the protein content was 15% of energy, the lipid content was 31% of energy and the carbohydrate content was 54% of energy.

Although the study was an uncontrolled, descriptive study, the results were very positive. All children showed significant improvement after 8 weeks of treatment. C-reactive protein returned to normal, serum albumin increased and the children increased in weight. Further, ideal biopsies indicated that 6 of the 7 children had reduced mucosal inflammation with 2 of the 6 children having complete healing. However, apart from the acid casein fraction, the enteral formula was an infant formula and not specifically targeted to patients with inflammatory conditions of the gastro-intestinal tract.

Therefore there is a need for an enteral composition which is based upon whole protein, which is targeted to patients which inflammatory conditions of the gastro-intestinal tract, and which is effective in the treatment or prophylaxis of inflammatory conditions of the gastro-intestinal tract.

SUMMARY OF THE INVENTION

Accordingly this invention provides an enteral, nutritional composition for the treatment or prophylaxis of inflammatory conditions of the gastro-intestinal tract, the composition comprising: (i) casein rich in TGF-β2; (ii) a lipid source providing about 35% to about 50% of energy: and (iii) a carbohydrate source.

The composition is found to be very palatable, avoiding the need for patients to take the composition via the naso-gastric route. Also, the composition is surprisingly effective in down-regulating major pathways of inflammation. Therefore the composition is a significant advance in the treatment or prophylaxis of inflammatory conditions of the gastro-intestinal tract.

Preferably the casein provides about 10% to about 14.5% of the energy of the composition; more preferably about 14% of the energy of the composition. Further, the casein preferably contains at least about 1.0 μg of TGF-β2 per g of casein; more preferably about 1.2 μg to about 2.0 μg of TGF-β2 per 8 of casein. For example, casein may contain about 1.4 μg to about 1.8 μg of TGF-β2 per g of casein.

The enteral, nutritional composition preferably contains about 10 μg to about 40 μg of TGF-β2 per 100 g of the composition, on a dry basis. More preferably, the enteral, nutritional composition contains about 20 μg to about 35 μg of TGF-β2 per 100 g of the composition, on a dry basis.

Preferably the lipid source comprises a mixture of medium and long chain triglycerides. For example, at least 20% by weight of the lipid source comprises medium chain triglycerides. More preferably, the lipid source comprises less than about 10% of total energy of essential fatty acids; even more preferably less than 5% of total energy of essential fatty acids.

The lipid source preferably provides about 38% to about 45% of energy; for example about 40% to about 42% of energy.

The carbohydrate source preferably provides about 35% to about 55% energy; for example about 40% to about 45% of energy. The carbohydrate source is preferably maltodextrin, corn starch or sucrose, or mixtures thereof.

The enteral, nutritional composition preferably contains low levels of sodium; for example from about 300 mg/l to about 600 mg/l.

The enteral, nutritional composition preferably has an energy content of about 800 kcal/l to about 1200 kcal/l; for example an energy content of about 1000 kcal/l.

In another aspect, this invention provides a method for the treatment or prophylaxis of inflammatory conditions of the gastro-intestinal tract, the method comprising administering to a patient an enteral, nutritional composition which comprises: (i) casein rich in TGF-β2; (ii) a lipid source providing about 35% to about 50% of energy; and (iii) a carbohydrate source.

Preferably the enteral, nutritional composition is administered as the sole source of nutrition. However it may also be used as feed supplement.

The inflammatory condition of the gastro-intestinal tract may be Crohn's disease. Preferably the patient is a patient undergoing treatment for the first time or who has not been treated for inflammatory conditions of the gastro-intestinal tract for more than about 1 year; preferably more than about 2 years.

BRIEF DESCRIPTION OF THE DRAWINGS

Embodiments of the invention are now described, by way of example only, with reference to the Figures in which.

DETAILED DESCRIPTION OF THE PREFERRED EMBODIMENTS

Figure 1A:
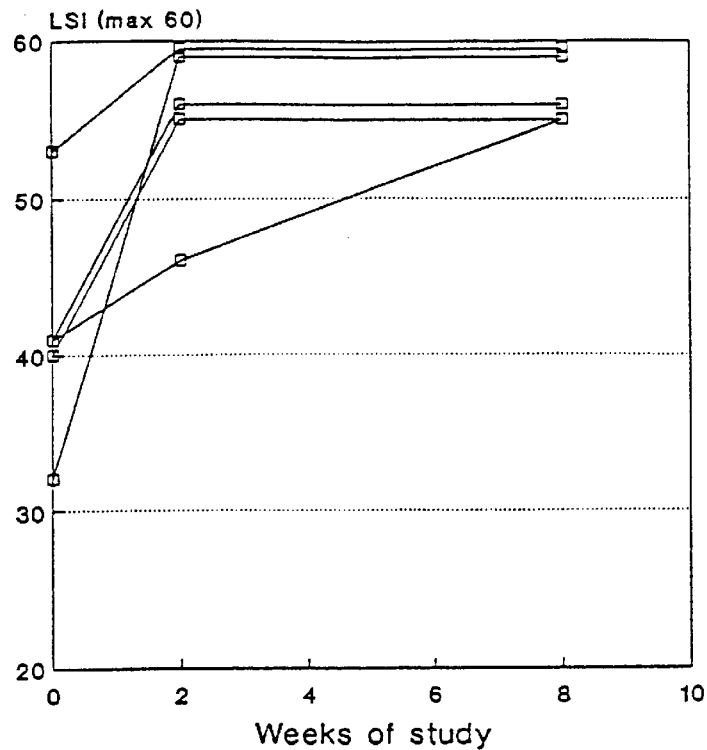
FIGS. 1a and 1b illustrate plots of Lloyd Still Index against treatment time for two groups of patients.

In this specification, the term enteral, nutritional composition means a composition which provides nutrition to a patient through the gastro-intestinal tract; for example by administration to the patient through the oral or nasogastric routes.

The enteral, nutritional composition is made up of casein which is rich in TGF-β2; a lipid source which provides about 35% to about 50% of the energy of the composition; and a carbohydrate source. The composition may be used in the treatment or prophylaxis of inflammatory conditions of the gastro-intestinal tract; for example in children, adolescents and adults.

The casein may be produced as is known in the art; for example as described in European patent application 0313515 and U.S. Pat. No. 5,461,033; the disclosures of which are incorporated by reference. The casein preferably contains about 1.2 μg to about 2.0 μg of TGF-β2 per g of casein; more preferably about 1.6 μg of TGF-β2 per g of casein. Further, the casein preferably provides about 10% to about 14.5% of the energy of the composition. For example, the protein source may provide about 14% of the energy of the composition. At these levels, the casein provides about 10 μg to about 40 μg TGF-β2 per 100 μg of the composition, on a dry basis. More preferably, the casein provides about 20 μg to about 35 μg of TGF-β2 per 100 g of the composition, on a dry basis. The casein may be provided in free form or in the form of a salt; for example a sodium salt.

Protein sources other than casein rear also be included in the composition as desired. These additional protein sources may be selected from, for example, milk protein, whey protein, soy protein, rice protein, pea protein and oat protein, or mixtures thereof. The form of these additional protein sources may be selected as desired. Also, free amino acids may be included.

The carbohydrate source provides about 35% to about 55% of the energy of the composition. For example, the carbohydrate source may provide about 45% of the energy of the composition. Several carbohydrates may be used including maltodextrin, corn starch, or sucrose, or mixtures thereof. Preferably the composition is free from lactose.

The lipid source includes a mixture of medium chain triglycerides (MCT) and long chain triglycerides (LCT). Preferably the lipid source provides about 35% to about 50% of the energy of the composition. For example, the lipid source may provide about 42% of the energy of the composition. The lipid profile may contain low levels of essential fatty acids (omega-3 and omega-6 fatty acids); preferably these polyunsaturated fatty acids provide less than about 10% of total energy of the lipid source. For example these polyunsaturated fatty acids may provide about 4% of total energy of total energy of the lipid source. Decreasing the levels of these polyunsaturated fatty acids is believed to decrease sensitivity to peroxydation; which may be beneficial in the treatment of inflammatory diseases.

The lipid source preferably includes at least about 30% to about 70% by weight of medium chain triglycerides. For example, medium chain triglycerides may make up about 50% to about 60% by weight of the lipid source. In addition to the absorption/tolerance benefits of a moderate content of long chain triglycerides, the composition is less likely to be immunosuppressive due to the low content of omega-6 fatty acids.

Suitable sources of long chain triglycerides are canola oil, soy oil, milk fat, corn oil and soy lecithin. Fractionated coconut oils are a suitable source of medium chain triglycerides. The lipid profile of the enteral composition is preferably designed to have a polyunsaturated fatty acid omega-6 (n-6) to omega-3 (n-3) ratio of about 4:1 to about 10:1. For example, the n-6 to n-3 fatty acid ratio may be about 6:1 to about 9:1.

The enteral composition preferably includes a complete vitamin and mineral profile.

The enteral composition may include a source of beta-carotene. Beta-carotene, formerly considered only as a precursor to vitamin A, is an important nutrient with anti-oxidant properties. For example, the composition may include about 0.5 to about 2.0 mg of beta-carotene per 1000 calories. This amount of beta-carotene is sufficient to maintain plasma beta-carotene concentration in the patient.

The enteral composition preferably contains reduced concentrations of sodium; for example from about 300 mg/l to about 400 mg/l. In particular, the sodium concentration may be about 350 mg/l. The remaining electrolytes may be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The enteral composition may be in the form of a soluble powder, a liquid concentrate, or a ready-to-use formulation. Ready to use formulations are particularly preferred. The composition may be fed to a patient via a nasogastric tube or by having the patient drink it. Various flavours, fibres and other additives may also be present.

The enteral composition may be used in the treatment or prophylaxis of inflammatory conditions of the gastro-intestinal tract; especially Crohn's disease. The enteral composition may form the sole source of nutrition during the period of treatment or may be supplemented with other food sources. Also in the prophylaxis of inflammatory conditions of the gastro-intestinal tract, the enteral composition may form a supplement to normal sources of food.

For the treatment or prophylaxis of inflammatory conditions, the amount of the enteral composition required to be fed to the patient will vary depending upon factors such as the risk and severity of the disease, the age of the patient, and whether the enteral composition is the sole source of nutrition. However the required amount may be readily set by a medical practitioner and would generally be in the range of about 25 kcal to about 45 kcal per kg of body weight per day. For example, the patient may be administered about 25 kcal to about 45 kcal per kg of body weight per day of the enteral composition. The enteral composition may be taken in multiple doses, for example 2 to 5 times to make up the required daily amount or may taken in a single dose.

EXAMPLE 1

A nutritional composition having the following constituents is prepared:

| Constituent | Unit | Per 100 Kcal | Per 100 g |
|---|---|---|---|
| Total energy | Kcal | 100 | 489 |
| Total fat | g | 4.71 | 23.0 |
| Total energy intake - fat | % | 42 | — |
| Total protein (casein) | g | 3.58 | 17.5 |
| Total energy intake - protein | % | 14 | — |
| Total carbohydrate | g | 11.0 | 54.0 |
| Total energy intake - CHO | % | 44 | — |
| Minerals (Ash) | g | 0.51 | 2.5 |
| sodium | mg | 35 | 170 |
| potassium | mg | 123 | 600 |
| chloride | mg | 75 | 365 |
| calcium | mg | 91 | 445 |
| phosphorous | mg | 61 | 300 |
| magnesium | mg | 20 | 100 |
| Vitamins including | | | |
| vitamin A | IU | 250 | 1200 |
| vitamin D | IU | 20 | 98 |
| vitamin E | IU | 1.5 | 7.3 |
| vitamin K1 | μg | 4.0 | 20 |
| vitamin C | mg | 8.0 | 39 |
| vitamin B1 | mg | 0.080 | 0.39 |
| vitamin B2 | mg | 0.13 | 0.64 |
| niacin | mg | 1.0 | 4.9 |
| vitamin B6 | mg | 0.10 | 0.49 |
| folic acid | μg | 20 | 98 |
| pantothenic acid | mg | 0.50 | 2.4 |
| vitamin B12 | μg | 0.40 | 2.0 |
| biotin | μg | 15 | 73 |

The constituents of the lipid source are as follows:

| Lipid Component | % By Weight of lipid | % of energy of composition |
|---|---|---|
| MCT's | 55.6 | 23 |
| Corn Oil | 26.1 | 11 |
| Milk fat | 13.9 | 6 |
| Soy lecithin | 4.4 | 2 |
| TOTAL | 100 | 42 |
| Short chain fatty acids | 14.4 | 26 |
| Mono unsaturated fatty acids | 5.4 | 11 |
| Poly unsaturated fatty acids | 2.8 | 5 |
| Essential fatty acids | 2.8 | |
| Linoleic acid | 2.5 | 4.6 |
| Linolenic | 0.3 | 0.5 |

The lipid source has a ω6 to ω3 ratio of about 9:1 and a cholesterol content of about 32.4 mg/100 g of solids.

EXAMPLE 2

Patients: Eleven children, of both sexes and between the ages of 5 to 19 years, are recruited for the study. All children have been diagnosed as suffering from Crohn's disease and the diagnosis has been confirmed by histology or radiology, or both. Children having significant stricture with prestenotic dilation and symptoms are rejected. The children are separated into two groups: Group 1 being made up of 5 children with active Crohn's disease who have not previously been treated or have been not been treated for 2 years; Group 2 being made up of 6 children with Crohn's disease in relapse and who have not been treated for 2 years except for 5 ASA derivatives.

Measurements: One week prior to commencement of the study, auxological data, school attendance, and pubertal status are determined for each child. Also, a dietary assessment of energy intake and content is made. One day prior to commencement, serum indicators of disease including C-reactive protein, erythrocyte sedimentation rate (ESR), platelet count, serum albumin, zinc plasma concentration and copper plasma concentration are measured. The same indicators are measured again after 2 weeks, 2 months, 4 months and 12 months. Further, 1.5 ml of blood is taken one day prior to commencement and again after 2 months, to measure the concentration of copper/zinc superoxide dismutase in red blood cells.

All children of group 1 are given barium meal and radiography is used to assess the disease site in the small bowel. All children of group 2 have had radiographic assessment of the disease site.

After the 8 weeks of treatment, all children are subjected to endoscopic assessment. A score of 0 to 3 (0=normal, 1=mild inflammation, 2=moderate inflammation, and 3=severe inflammation) is assigned to each area of the bowel which is inspected: being the terminal ileum, caecum, descending colon, transverse colon, ascending colon, sigmoid colon and rectum. Also, a histological score of 0 to 3 (0=normal, 1=mild inflammation, 2=moderate inflammation, and 3=severe inflammation) is assigned to each site biopsied.

An immunological assessment is made upon commencement of the study and after 8 weeks. The immunological parameters measured are: (i) epidermal growth factor in plasma, (ii) tumour necrosis factor and neutrophil elastase in stools, (iii) tumour necrosis factor, IFN-γ, IL1-β, IL2, IL5, IL8 and IL10 in tissue (by mucosal biopsies). Also, the presence of pS2 and hsp peptides are determined by in situ hybridization. A blood sample is also drawn after 2 weeks of treatment for the measurement of epidermal growth factor.

Further, a modified Lloyd Still Index of clinical disease activity is determined for each patient (Lloyd-Still et al; 1979; *Dig. Dis. Sci;* 24: 620–24). A maximum score of 60 points is obtained for no disease activity.

Treatment: Each child in the study is fed the nutritional composition of example 1 as the sole source of nutrition for a period of 8 weeks. After the 8 weeks, each child undergoes a period of food reintroduction over 4 weeks. Administration of the nutritional composition is under the supervision of a pediatric dietician and is effected orally or by nasogastric tube as desired by the patient. The intake of the nutritional composition is adjusted on the basis of tolerance, palatability and weight gain.

Results
Endoscopic assessment, Main Initial Disease Site and Outcome

| Group | Patient | Organ | Endoscopic Assessment at start | Endoscopic Assessment after 8 weeks |
|---|---|---|---|---|
| 1 | 1 | Terminal ileum | 3 | 1 |
|   | 2 | Terminal ileum | 2 | 2 |
|   |   | Colon | 2 | 1 |
|   | 3 | Terminal ileum | 2 | 1 |
|   |   | Caecum | 0 | 1 |
|   | 4 | Terminal ileum | 3 | 2 |
|   |   | Caecum | 2 | 1 |
|   |   | Ascending colon | 2 | 0 |
|   | 5 | Rectum | 1 | 1 |
| 2 | 1 | Terminal ileum | 2 | 0 |
|   | 2 | Terminal ileum | 3 | Did not complete Study |
|   |   | Transverse colon | 3 |  |
|   |   | Sigmoid | 1 |  |
|   | 3 | Terminal ileum | 2 | 0 |
|   |   | Rectum | 0 | 1 |
|   | 4 | Transverse colon | 1 | 1 |
|   | 5 | Caesum | 3 | Did not complete Study; appendix abscess |
|   |   | Ascending colon | 3 |  |
|   |   | Transverse colon | 2 |  |
|   |   | Descending colon | 2 |  |
|   | 6 | Terminal ileum | 2 | 1 |
|   |   | Descending colon | 1 | 0 |
|   |   | Sigmoid | 1 | 0 |

In general, apart from patients who did not complete the study, all patients have an improved endoscopic assessment.

| Group | Patient | Main Initial Disease Site | Outcome |
|---|---|---|---|
| 1 | 1 | Terminal ileum | Full remission at 2 and 4 months |
|   | 2 | Terminal ileum, Colon | Full remission at 2 and 4 months |
|   | 3 | Terminal Ileum, caecum | Full remission at 2 and 4 months |
|   | 4 | Terminal Ileum, caecum | Full remission at 2 and 4 months; relapse at 8 months |
|   | 5 | Rectum | Full remission at 2 and 4 months |
| 2 | 1 | Terminal Ileum | Full remission at 2 and 4 months |
|   | 2 | Terminal Ileum, colon | Failed to complete treatment, appendix abscess |
|   | 3 | Terminal Ileum | Full remission at 2 and 4 months |
|   | 4 | Transverse colon | Full remission at 2 and 4 months |
|   | 5 | Colon, Caecum | Failed to complete treatment, severe colonic disease |
|   | 6 | Terminal Ileum, colon | Full remission at 2 months, relapsed at 4 months |

The results indicate that the treatment was effective in bringing about remission in most cases; especially with the patients who had not previously been treated. Further, the relapse rate is low.

Tolerance and Energy Intake

Prior to treatment, 4 of the patients consumed between 75 to 100% of necessary energy 3 of the patients consumed between 50 to 75% of necessary energy, 3 of the patients consumed less than 50% of necessary energy, and 1 was not determined.

After 2 weeks of treatment, 6 of the patients consume 100% of necessary energy, 3 of the patients consumed between 90 to 100% of necessary energy, and 2 of the patients consumed less than 90% of necessary energy. Therefore the treatment results in a beneficial increase in energy consumption.

After 2 weeks of treatment, 7 of the patients are able to tolerate the nutritional composition well, 2 of the patients are able to tolerate the nutritional composition adequately, and 1 patient is only able to poorly tolerate the nutritional composition.

Lloyd Still Index of Clinical Disease Activity

Figure 1B:
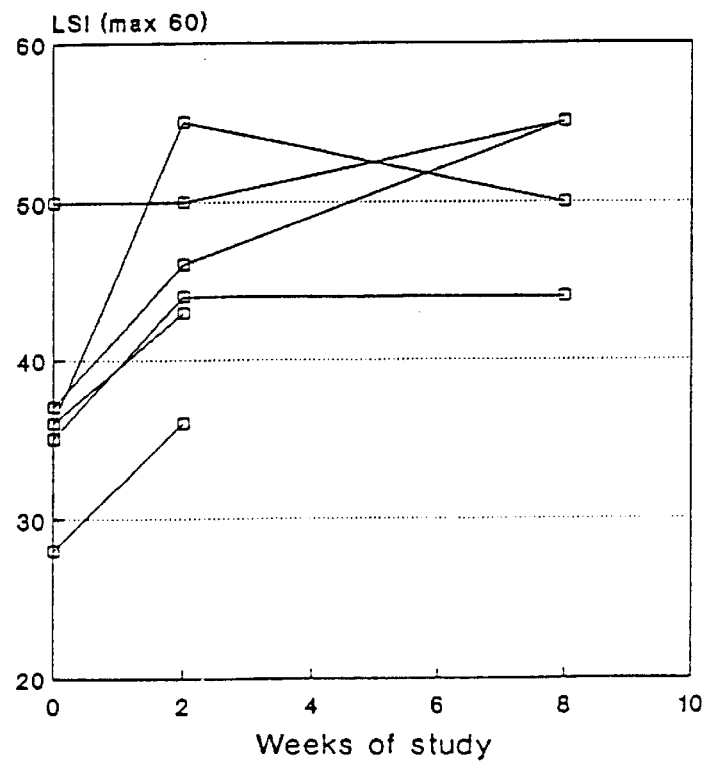

The Lloyd Still Index for the patients are illustrated in FIGS. 1a and 1b. The patients of Group 1 all have a substantially improved Lloyd Still Index. The patients of Group 2 in general have an improved Lloyd Still Index but to less of an extent.

Erythrocyte Sedimentation Rate (ESR)

Figure 2A:
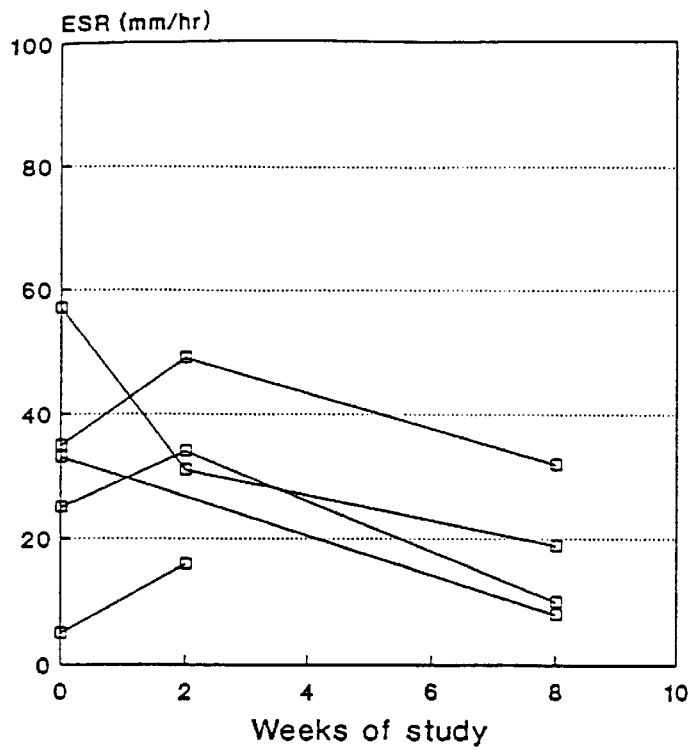
FIGS. 2a and 2b illustrate plots of Erythrocyte sedimentation rate against treatment time for two groups of patients.
Figure 2B:
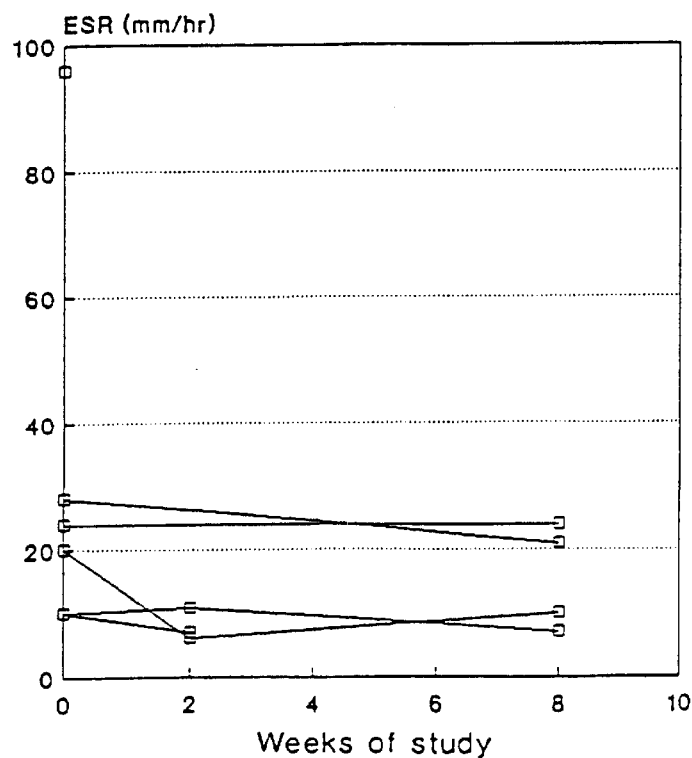

The ESR for the patients are illustrated in FIGS. 2a and 2b. The patients in general have an improved ESR after treatment.

Serum Albumin

Figure 3A:
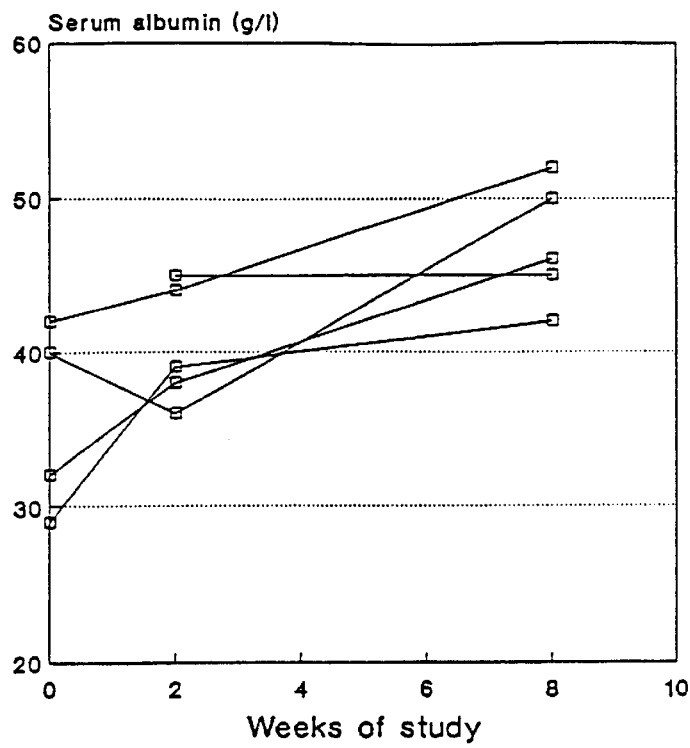
FIGS. 3a and 3b illustrate plots of serum albumin levels against treatment time for two groups of patients.
Figure 3B:
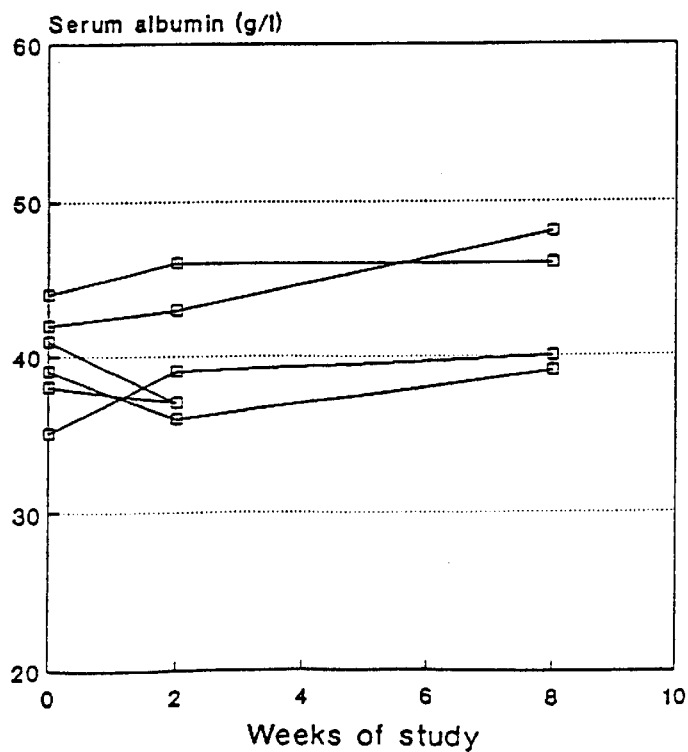

The serum albumin levels of the patients are illustrated in FIGS. 3a and 3b. For the patients of group 1, the serum albumin levels increase with treatment. For the patients of group 2, the serum albumin levels remain substantially constant or increase with treatment. Since increased levels of serum albumin are a strong marker of reduced inflammation, the patients of group 1 are characterised as having reduced inflammation.

Immunological Assessment

Figure 4:
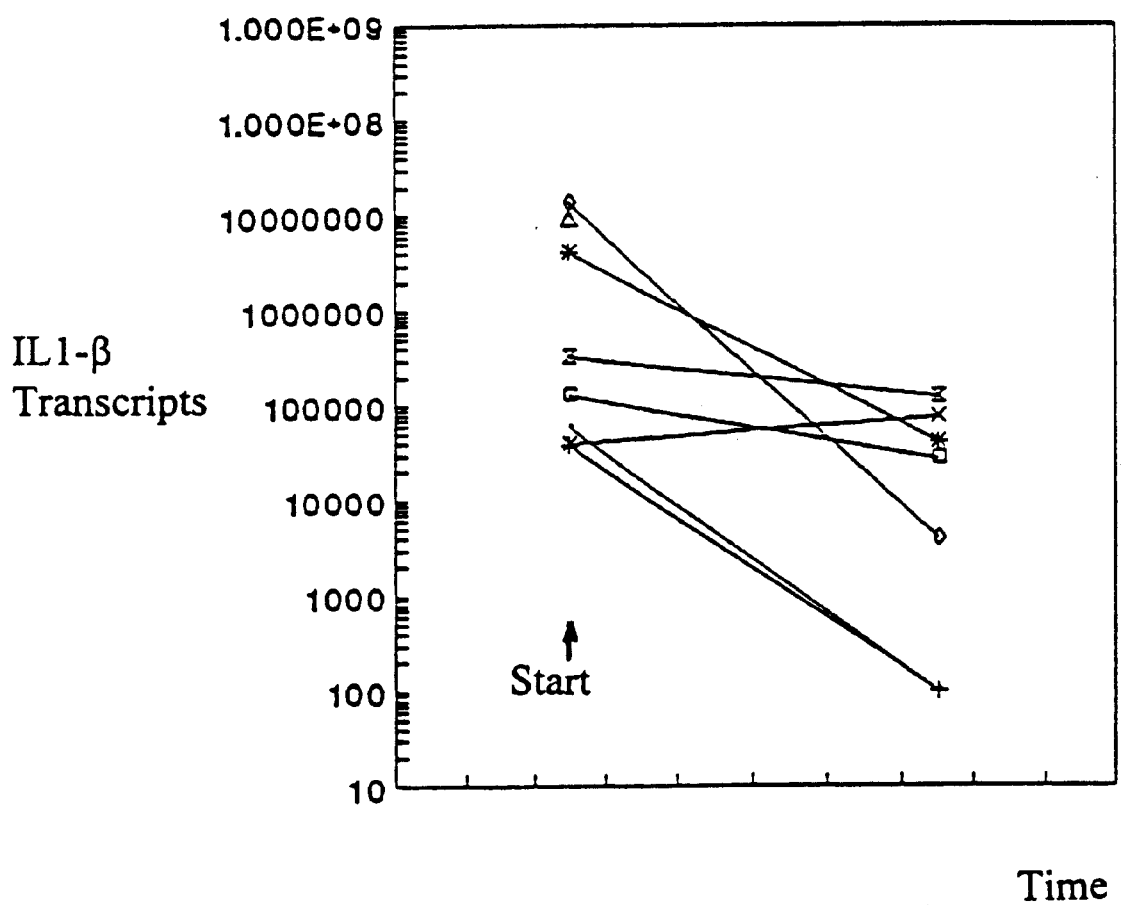
FIG. 4 illustrates a plot of IL1-β transcription against treatment time.

Levels of IL1-$\beta$ for 8 of the patients who completed the study are illustrated in FIG. 4. Seven of the patients have reduced IL1-$\beta$ levels after the treatment; one patient has marginally increased levels. Increased levels of IL1-$\beta$ are a strong marker of inflammation and hence reduced levels are a strong indicator of down regulation of inflammatory response. Therefore most patients have significantly reduced inflammatory response.

We claim:

1. An enteral, nutritional composition for the treatment or prophylaxis of inflammatory conditions of the gastro-intestinal tract, the composition comprising: casein rich in TGF-$\beta$2; a lipid source providing about 35% to about 50% of energy and containing a mixture of medium and long chain triglycerides; a carbohydrate source; and the composition having an energy content of at least about 800 Kcal/l.

2. A composition according to claim 1 in which the casein provides about 10% to about 14.5% of the energy of the composition.

3. A composition according to claim 1 in which the casein contains about 1.2 $\mu$g to about 2.0 $\mu$g of TGF-$\beta$2 per g of casein.

4. A composition according to claim 1 which contains about 10 $\mu$g to about 40 $\mu$g of TGF-$\beta$2 per 100 g of the composition, on a dry basis.

5. A composition according to claim 1 in which the medium chain triglycerides provide at least about 20% by weight of the lipid source.

6. A composition according to claim 5 in which the lipid source comprises less than about 10% of lipid energy of polyunsaturated essential fatty acids.

7. A composition according to claim 1 in which the lipid source provides about 38% to about 45% of energy.

8. A composition according to claim 1 which contains from about 300 mg/l to about 600 mg/l of sodium.

9. A composition according to claim 1 which has an energy content of about 800 kcal/l to about 1200 kcal/l.

10. An enteral, nutritional composition for the treatment or prophylaxis of inflammatory conditions of the gastro-intestinal tract, the composition comprising: a protein source including casein which contains at least about 10 µg of TGF-β2 per g of casein; a lipid source providing about 35% to about 50% of energy and containing a mixture of medium and long chain triglycerides; a carbohydrate source; and the composition having an energy content of at least about 800 Kcal/l.

11. A composition according to claim 10 in which the casein provides about 10% to about 14.5% of the energy of the composition.

12. A composition according to claim 10 in which the casein contains about 1.2 µg to about 2.0 µg of TGF-β2 per g of casein.

13. A composition according to claim 1 in which the medium chain triglycerides provide at least about 20% by weight of the lipid source.

14. A composition according to claim 13 in which the lipid source comprises less than about 10% of lipid energy of polyunsaturated essential fatty acids.

15. A composition according to claim 10 which contains from about 300 mg/l to about 600 mg/l of sodium.

16. A composition according to claim 10 which has an energy content of about 800 kcal/l to about 1200 kcal/l.

17. A method for the treatment or prophylaxis of inflammatory conditions of the gastro-intestinal tract, the method comprising administering to a patient an enteral, nutritional composition which comprises: casein rich in TGF-β2; a lipid source providing about 35% to about 50% of energy and containing a mixture of medium and long chain triglycerides; a carbohydrate source; and the composition having an energy content of at least about 800 Kcal/l.

18. A method according to claim 17 in which the casein contains about 1.2 µg to about 2.0 µg of TGF-β2 per g of casein.

19. A method according to claim 17 which contains about 10 µg to about 40 µg of TGF-β2 per 100 g of the composition, on a dry basis.

20. A method according to claim 17 in which the medium chain triglycerides provide at least about 20% by weight of the lipid source.

21. A method according to claim 20 in which the lipid source comprises less than about 10% of lipid energy of polyunsaturated essential fatty acids.

22. A method according to claim 17 in which the inflammatory condition of the gastro-intestinal tract is Crohn's disease.

23. A method according to claim 17 in which the patient is a patient undergoing treatment for the first time or who has not been treated for inflammatory conditions of the gastro-intestinal tract for more than about 1 year.

* * * * *